Figure 1A:
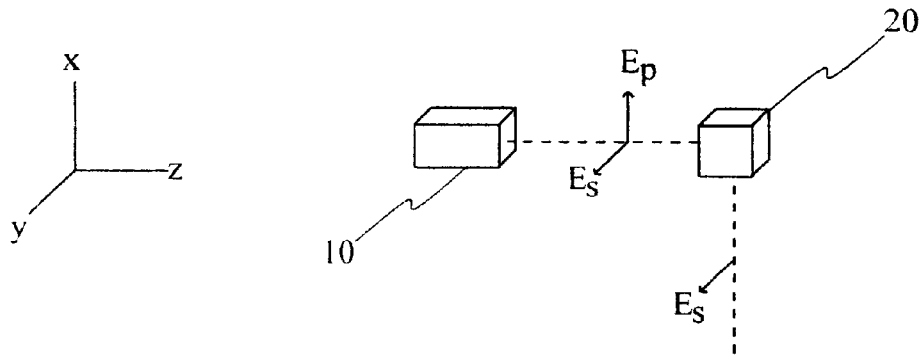

United States Patent [19]
Sipilä

[11] Patent Number: 6,049,589
[45] Date of Patent: Apr. 11, 2000

[54] X-RAY FLUORESCENCE MEASURING SYSTEM MAKING USE OF POLARIZED EXCITATION RADIATION, AND X-RAY TUBE

[75] Inventor: Heikki Sipilä, Espoo, Finland

[73] Assignee: Metorex International Oy, Espoo, Finland

[21] Appl. No.: 09/103,389

[22] Filed: Jun. 24, 1998

[30] Foreign Application Priority Data

Jun. 26, 1997 [FI] Finland ................................ 972755

[51] Int. Cl.[7] .............................................. H01J 35/08
[52] U.S. Cl. .......................................... 378/143; 378/144
[58] Field of Search ..................................... 378/143, 144

[56] References Cited

U.S. PATENT DOCUMENTS

| | | | |
|---|---|---|---|
| 2,168,780 | 8/1939 | Olshevsky . | |
| 2,922,904 | 1/1960 | Zunick . | |
| 3,752,989 | 8/1973 | Motz et al. | 378/143 |
| 3,944,822 | 3/1976 | Dzubay | 378/145 |
| 4,637,042 | 1/1987 | Braun | 378/143 |
| 4,799,250 | 1/1989 | Penato et al. | 378/144 |

FOREIGN PATENT DOCUMENTS

| | | |
|---|---|---|
| 0639766A1 | 2/1995 | European Pat. Off. . |
| 72814 | 3/1987 | Finland . |
| 264360A | 2/1989 | Germany . |
| 58-108637A | 6/1983 | Japan . |
| 2025040A | 1/1980 | United Kingdom . |

OTHER PUBLICATIONS

G. Pavlovskaya etal., "Source of Nanosecond Soft X–Ray Pulses," Instruments and Experimental Techniques, vol. 17, No. 5, pp. 1478–1480 (1975).

*Primary Examiner*—Craig E. Church
*Attorney, Agent, or Firm*—Rockey, Milnamow & Katz, Ltd.

[57] ABSTRACT

The invention relates to X-ray fluorescence measuring systems, more specifically to methods for producing polarized X-radiation. The invention is based on the idea of using beryllium as the anode material despite its poor effectiveness. Some of the X-radiation spectrum produced by a beryllium anode is polarized radiation, more specifically its high-energy portion. The system of the invention involves filtering out the low-energy portion of the spectrum, whereby the remaining intensely polarized radiation can be used as excitation radiation in X-ray fluorescence measurements. The system of the invention is capable of achieving a certain intensity of polarized X-radiation by means of an X-ray tube less powerful than those used in common prior art solutions based on the use of scattering media.

7 Claims, 4 Drawing Sheets

X-RAY FLUORESCENCE MEASURING SYSTEM MAKING USE OF POLARIZED EXCITATION RADIATION, AND X-RAY TUBE

The present invention relates to X-ray fluorescence measuring systems, more specifically to methods for producing polarized X-radiation.

In X-ray fluorescence analysis, the sensitivity of measurements is limited by background radiation emerging from a specimen or sample being examined. Most of the background radiation is a result of the scattering of a radiation-source emitted excitation radiation to a detector. When using wide-band excitation radiation, the excitation radiation scattered from a specimen is perceived as a powerful background radiation. The excitation radiation also includes some fluorescence radiation originating from the materials of the X-ray tube used, and other components of a measuring system, such as possible collimators, also create fluorescence radiation. The impact of these sources of background radiation can be reduced by minirizing the scattering of excitation radiation to a detector by using polarized excitation radiation. This is described in more detail with reference to FIGS. 1a and 1b.

When evenly polarized X-radiation scatters from a medium, it is concurrently polarized. The polarization of scattered radiation varies in terms of intensity and direction according to a given scattering angle. A radiation scattered at an angle of 90° relative to the incoming radiation is polarized in a direction perpendicular to a plane defined by the directions of incoming radiation and scattered radiation. The portion of incoming radiation polarized in other directions is almost completely eliminated.

This is depicted in FIG. 1a. A radiation source 10 emits in all directions polarized radiation, which scatters from a scatterer 20. Naturally, some radiation scatters in every direction, but this discussion only deals with radiation scattered at an angle of 90°. The radiation scattered at a right angle is intensely polarized in a direction $E_s$ perpendicular to a plane defined by the direction of incoming radiation and the direction of scattered radiation. A portion $E_p$ of incoming radiation polarized in parallel with said plane does not, in an ideal case, scatter at all at an angle of 90°.

Figure 1B:
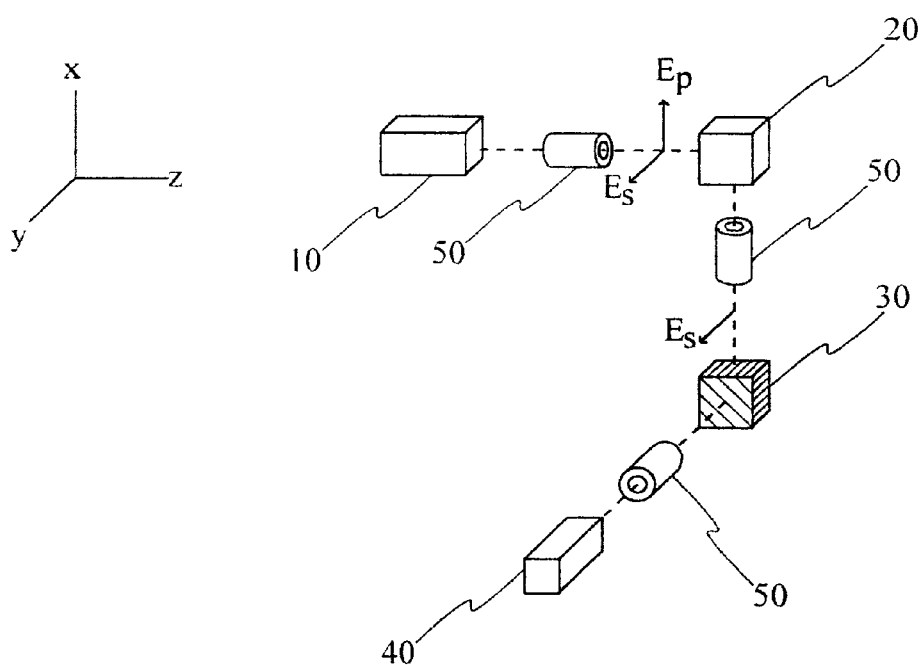

The polarization of scattered radiation can be exploited in a measuring system, e.g. as shown in FIG. 1b. The figure depicts a system, wherein the polarized excitation radiation scattered by a scatterer 20 is carried to a specimen 30 and the fluorescence radiation created by the excitation radiation is studied by means of a detector 40. A typical measuring system also involves the use of collimators 50. When a detector is positioned relative to a specimen in such a way that a straight line defined by the detector and the specimen extends perpendicularly to a plane defined by the direction of excitation radiation produced by a radiation source 10 and radiation scattered by the scatterer 20, there is no excitation radiation in an ideal case scattering at all from the specimen 30 to the detector 40. This results from the fact that the specimen 30 only receives polarized excitation radiation, scattered from the scatterer 20 and having a direction of polarization parallel to a plane defined by the scatterer 20, the specimen 30, and the detector 40. According to the principle shown in FIG. 1a, the radiation polarized in this fashion is eliminated from the radiation scattered from the specimen 30 towards the detector and, thus, in an ideal case, no radiation at all scatters from the specimen 30 in the direction towards the detector 40. Thus, the fluorescence radiation emerging from the specimen 30 is more distinctly perceivable.

One drawback in such a structure is a poor effectiveness. In order to make the scattering radiation as completely polarized as possible, the scattering angle must be as close as possible to the right angle, whereby the collimators must delimit the beam in each range to be as narrow as possible. However, the narrowing of a beam reduces intensity of the beam. This can be compensated for by increasing the power of the radiation source 10, but this results in a rapid increase of the price of the apparatus. Methods like the one shown in FIG. 1b are described in more detail e.g. in the article Richard W. Ryon and John D. Zahrt, "Poarized Beam X-ray Fluorescence", Advances in X-ray Analysis, vol 38, pp. 491–515, 1994.

The basic structure of FIG. 1b has been subjected to various modifications for improved effectiveness. One solution makes use of a portion of excitation radiation passed through the scatterer 20, which is carried to a secondary target where it produces fluorescence radiation. This fluorescence radiation scatters from the scatterer 20, thus increasing the intensity of polarized radiation scattered towards a specimen. Such mechanisms are described e.g. in the publication Igor Tolonnikoff, "Geometric considerations in EDXRF to increase fluorescence intensities and reduce background", Advances in X-ray Analysis, vol. 35, p. 1009, 1992.

The above-cited publications also disclose other types of scattering geometries, such as circular geometry, for producing polarized radiation. By using scatterers it is possible to achieve a substantially continuous excitation radiation spectrum. A drawback in all these solutions is, however, that a specimen being examined is supplied with radiation scattered in a scattering medium external of the radiation source, the radiation arriving at the specimen having an intensity which is a small fraction of the intensity of the radiation source.

Polarized radiation can also be produced by means of a suitable lattice chosen according to wavelength, using the Bragg's diffraction. At low energies, it is possible to use laminated structures dimensioned according to wavelength. At high energies, the lattice must be made of a crystalline material. This type of solution only produces a single-wavelength radiation, limiting its possible applications. This type of solution is also hampered by the same drawback as those based on the use of a scattering medium, namely a poor effectiveness, since most of the radiation energy produced by a radiation source will be eliminated.

Figure 2A:
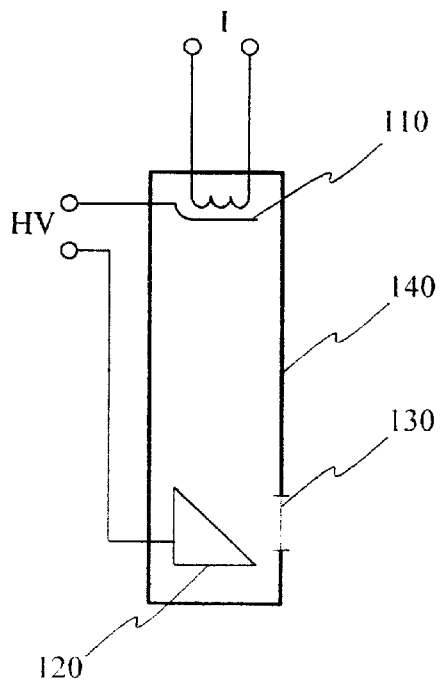
Figure 2B:
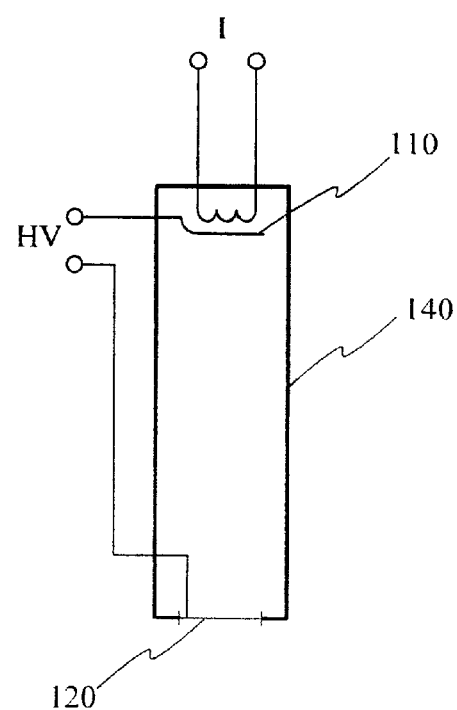

One excellent source of polarized X-radiation is synchrotron radiation. Synchrotron radiation is inherently polarized and has a very high intensity, which is why synchrotron radiation is almost ideal excitation radiation in terms of X-ray fluorescence measurements. However, synchrotrons are extremely bulky and expensive pieces of equipment, which is a major restriction to the commercial use and applications thereof. Therefore, those are best suitable primarily for basic scientific research. The production of X-radiation is typically effected by means of X-ray tubes. The following description deals briefly with the basic structure of conventional X-ray tubes. FIGS. 2a and 2b illustrate two conventional basic types of an X-ray tube. The mechanism of FIG. 2a is typical when using a thick anode. An X-ray tube cathode 110 is heated by means of a filament and electric current 1 and a high voltage HV is coupled between the cathode 110 and an anode 120. The electrons emitted from the cathode 110 accelerate in an electrical field between the cathode and the anode and collide with the anode. Upon colliding with anodic atoms, the electrons loose their kinetic energy in one or more collisions, producing e.g. decelerating radiation. The electrons also serve to excite the atoms of the anode material, whereby the deexcitation of excited conditions results in the emission of characteristic X-radition. The resulting X-radiation is delivered from the X-ray tube by way of a window 130 included in a tube housing 140. The window consists typically of a thin film of some lightweight metal, generally beryllium, which has a very simple spectrum and is thus readily separable from the results of measurements made by means of the radiation produced by the X-ray tube.

The basic structure of FIG. 2b involves the use of a thin, so-called transmission anode. In such a structure, the anode 120 functions also as a window. In the most typical solution, the anode consists of a thin metal layer on top of a carrier material functioning as the actual window. Conventionally, the carrier material in transmission anodes comprises a beryllium membrane, on the surface of which is provided a thin layer of a heavier metal, such as scandium, functioning as the actual anode.

Patent publications DD 264 360 and DD 273 332 disclose the use of beryllium as an actual anode material. An object in the solution disclosed in the cited publications is to provide an X-ray spectrum as simple as possible, since the use of a heavier metal as the anode material complicates significantly the resulting radiation spectrum. A second object in the cited solutions is to achieve a simple X-ray tube configuration. However, the X-radiation produced by an anode material has an intensity which is roughly proportional to the square of the atomic number of a material. Thus, such solutions have a drawback in poor effectiveness, which is why a light element, such as beryllium, is not usually employed as the anode material. As pointed out above, the anode material comprises typically a heavier metal, such as scandium, producing an improved intensity.

Polarized radiation can also be produced directly by means of an X-ray tube, without an external polarizing element. The radiation produced by an electron in a single collision is polarized and, thus, polarized decelerating radiation appears when using a very thin anode as most of the electrons only collide once with atoms of the anode material.

The spectrum of decelerating radiation produced by thick anodes is weighted on the low-energy end of the spectrum. In this part of the spectrum, the radiation is also polarized in all directions, since the low-energy decelerating radiation develops as the electron gradually decelerates as a result of several collisions. Polarized radiation appears in a some degree in the higher-energy end of the radiation spectrum, wherein the radiation originates from electrons that have lost most of their kinetic energy in a single collision. However, the share of polarized radiation decreases dramatically as the ordinal number of the anode material increases. In the abovecited article by Ryon and Zahrt, it is indeed pointed out that the production of polarized radiation by means of a scattering medium has in practice proved the most effective method.

The polarization of X-radiation produced by various materials is examined in more detail e.g. in the article Paul Kirkpatrick and Lucille Wiedmann, "Theoretical Continuous X-Ray Energy and Polarization", Physical Review 67 (1945) 321.

An object of the invention is to provide a source of polarized X-radiation, which is more simple than prior known technology. Another object of the invention is to provide a source of polarized X-radiation, which is more effective than prior art solutions based on a scattering medium. Still another object of the invention is to provide an X-ray fluorescence measuring system, which is more simple than prior art solutions.

The objects are achieved by using beryllium as the anode material of an X-ray tube and by filtering the low-energy portion of the spectrum out of the resulting X-radiation, which leaves a strongly polarized high-energy portion of the spectrum highly suitable for excitation radiation. The use of such a source of polarized X-radiation results in a simple X-ray fluorescence measuring system, reducing the size of apparatus and lowering the price of apparatus.

The X-ray fluorescence measuring system of the invention is characterized in that at least a certain portion of an X-ray tube anode in the system, against which the electrons separating from the cathode of said X-ray tube are adapted to collide, is made essentially from beryllium for producing at least partially polarized X-radiation, and that the system further comprises a filter for eliminating at least partially a poorly polarized spectral portion of the at least partially polarized X-radiation.

The invention relates also to an X-ray tube, which is characterized in that at least a certain portion of its anode, against which the electrons separating from the cathode are adapted to collide, is made essentially from beryllium for producing at least partially polarized Xradiation, and that it further comprises a filter for eliminating at least partially a poorly polarized spectral portion of said at least partially polarized X-radiation.

The invention relates also to the use of a beryllium-anode equipped X-ray tube for producing polarized X-radiation.

The invention is based on the idea of using beryllium as the anode material despite its poor effectiveness. Some of the X-radiation spectrum produced by a beryllium anode consists of polarized radiation, more specifically its high-energy portion. The system of the invention is used to filter out the low-energy portion of the spectrum, whereby the remaining intensely polarized radiation can be used as excitation radiation in X-ray fluorescence measurements. The system of the invention is capable of achieving a certain intensity of polarized X-radiation by means of an X-ray tube less powerful than those used in common prior art solutions based on the use of scattering media.

Figure 3:
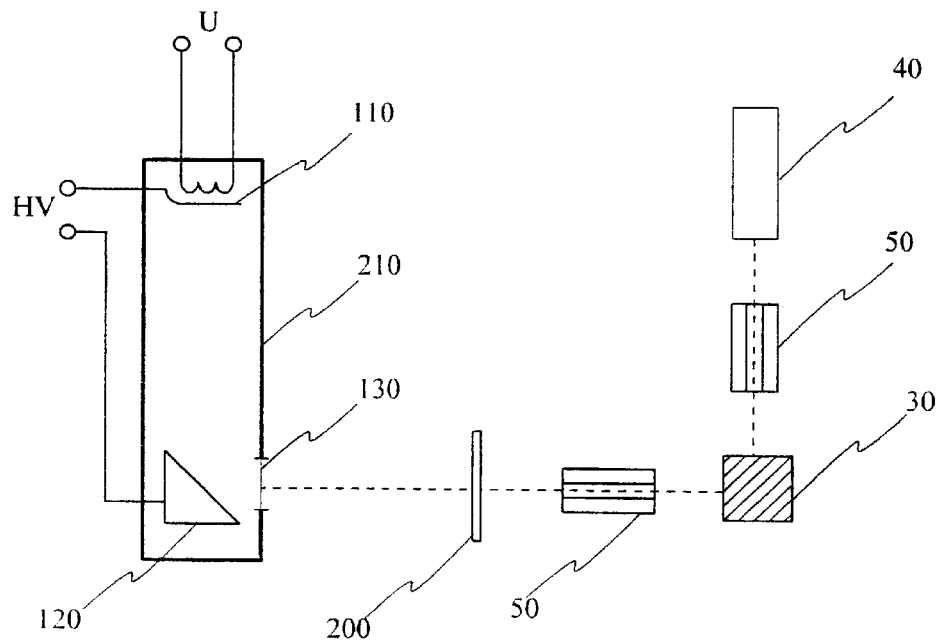
Figure 4:
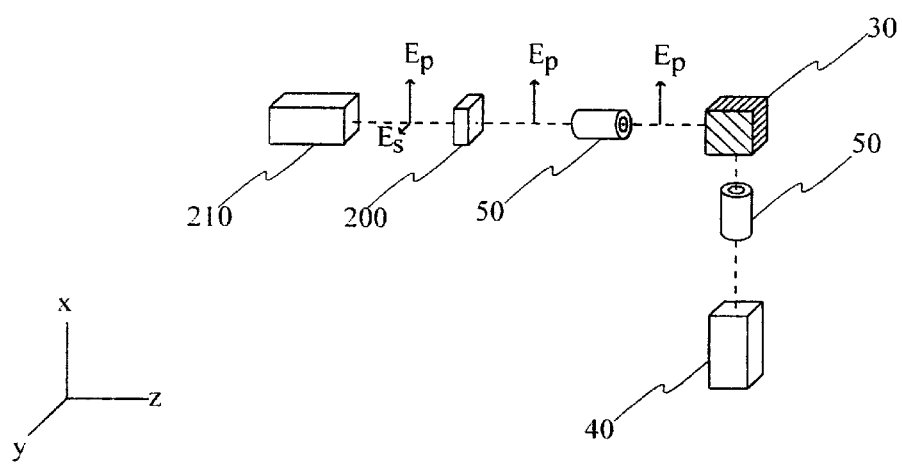
Figure 5A:
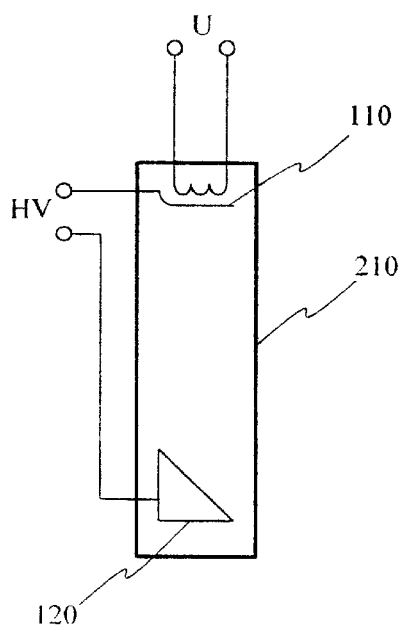
Figure 5B:
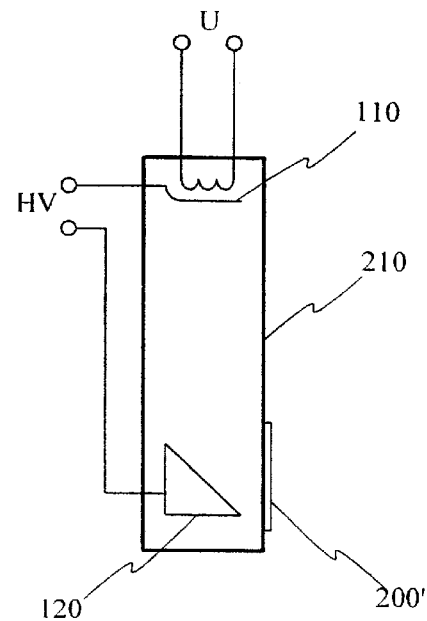

The invention will now be described in more detail with reference made to the accompanying drawings, in which FIG. 1a depicts the polarization of X-radiation in scattering, FIG. 1b shows a polarized X-ray fluorescence measuring system based on the use of a scattering medium, FIG. 2a shows a basic structure for a conventional X-ray tube, FIG. 2b shows another basic structure for a conventional X-ray tube, FIG. 3 shows one X-ray fluorescence measuring system of the invention, FIG. 4 illustrates polarization levels of radiation occurring in the X-ray fluorescence measuring system of FIG. 3, FIG. 5a shows one X-ray rube configuration of the invention, and FIG. 5b shows another X-ray tube configuration of the invention.

In the figures, the same reference numerals and symbols are used for corresponding components.

FIG. 3 shows one X-ray fluorescence measuring system of the invention. An X-ray tube 210 includes an anode 120 made of beryllium. Alternatively, the anode can be made of some other material as well, having its surface provided with a beryllium layer. The electrons, emerging from a cathode 110 and accelerated by a high voltage HV, collide with beryllium on the anode 120 to produce X-radiation. This X-radiation is delivered out of the X-ray tube by way of a window 130, whereafter a given portion thereof is separated from the high-energy end of the radiation spectrum. This given portion may be constituted e.g. by the top 20% of the essential wavelength band of the spectrum. Downstream of a filter, the radiation is carried through a collimator 50 to a specimen 30, wherein this radiation excites fluorescence radiation. The radiation emerging from the specimen 30 is carried through a second collimator 50 to a detector 40.

FIG. 4 illustrates the action of such a measuring system the same way as FIG. 1. The radiation produced by the beryllium-anode equipped X-ray tube 210 manifests all directions of polarization, represented in FIG. 4 by vectors $E_p$ and $E_s$. However, the polarization of radiation produced by such an X-ray tube has the previously described energy dependence and, thus, by eliminating the low-energy spectral portion from the radiation by means of a filter 200, there will only remain essentially an intensely polarized high-energy portion of the spectrum, which is polarized in the direction $E_p$. When this polarized radiation is delivered to the specimen 30 and the detector is positioned in such a way that the polarization direction $E_p$ coincides with a plane defined by the X-ray tube 210, the specimen 30, and the detector 40, the excitation radiation coming from the X-ray tube has its scattering to the detector at a minimum. Hence, such a system can be used for minimizing the amount of excitation radiation scattered directly to the detector for a more accurate perception of the fluorescence radiation emitted by the specimen 30.

In the measuring system depicted in FIGS. 3 and 4, one or more collimators can also be positioned between the X-ray tube 210 and the filter 200.

As pointed out previously in reference to FIG. 3 the anode 120 can be provided with a housing made of some material other than beryllium and the node housing can be coated with a beryllium layer. At energies conventionally used in X-ray tubes, the stopping distance for an electron in beryllium is a few tenths of a millimeter and, thus, the beryllium layer need not necessarily be thicker than a few tenths of a millimeter.

The production of polarized X-radiation can also be carried out by using an X-ray tube provided with a transmission anode. In this type of embodiment, the anode is substantially constituted by beryllium and provides a window for the X-ray tube.

In one preferred embodiment of the invention, the filter 200 is an integral part of the X-ray tube 210. The filter 200 can be secured by some prior known technique e.g. to the housing of an X-ray tube at a suitable distance from the X-ray tube window or also in contact with the window. According to a target to be examined, a suitable filter material may be such that the fluorescence radiation created thereby does not fall on a spectral area being examined. A few possible materials include e.g. titanium, steel, and molybdenum. In one preferred embodiment of the invention, the housing material of the X-ray tube constitutes at least a portion of the filter 200. In this type of embodiment, the X-ray tube need not include a separate window at all, as illustrated in FIG. 5a. No separate filter is needed, either, if the housing material can be selected in such a way that its filtering capabilities are sufficient for a desired application. In case the housing material is not able to filter the decelerating radiation completely as desired, the surface of the X-ray tube housing can be provided with one or more extra layers 200' of a suitable material for an optimized filtering, as illustrated in FIG. 5b.

The solution of the invention is generally applicable to all X-ray fluorescence measurements but, by virtue of its sensitivity, particularly to the analysis of extremely low concentrations of heavy metals. The solution is capable of achieving a very high sensitivity, for example, in the analysis of the K-lines of gold, of achieving a sensitivity of even less than 1 ppm. The solution of the invention also enables for example the analysis of lead by means of L-lines even from a living tissue, which enables the analysis of lead accumulating in human tissues, especially in bones. The solution of the invention can also be used advantageously for the analysis of very low concentrations of gold, platinum, as well as rare earth metals, for example in mining applications. One noteworthy preferred application is also a heavy metal analysis, not only for tissue measurements but also from the environment, such as waterways.

The filter 200 may comprise any filter known in the prior art.

The measuring system of the invention is remarkably simpler than the prior art solutions. The measuring system of the invention need not be provided with a separate scatterer for producing polarized radiation. The measuring system of the invention is superior in terms of effectiveness, whereby it is sufficient to use a less powerful X-ray tube for producing a polarized radiation power of a given strength than those used in the prior art solutions. For these reasons, the measuring system of the invention is more compact and less expensive to manufacture than the corresponding prior art X-ray fluorescence measuring systems making use of polarized radiation.

The invention has been described above with reference to a few preferred embodiments thereof, but it is obvious that the invention can be modified in a variety of ways within the scope of the inventional concept defined by the annexed claims.

I claim:

1. An X-ray fluorescence measuring system, comprising an X-ray tube for producing excitation radiation and a detector for measuring fluorescence radiation emitting from a target to be examined, wherein
    at least a certain portion of an anode of said X-ray tube, against which the electrons separating from the cathode of said X-ray tube are adapted to collide, is made essentially from beryllium for producing at least partially polarized X-radiation, and that
    the system further comprises a filter for eliminating at least partially a poorly polarized spectral portion of the at least partially polarized X-radiation.

2. A system as set forth in claim 1, wherein the anode of said X-ray tube is made completely of beryllium.

3. An X-ray tube comprising an anode and a cathode for producing polarized radiation, wherein at least a certain portion of the anode, against which the electrons separating from the cathode are adapted to collide, is made essentially from beryllium for producing at least partially polarized X-radiation, and in that
    the X-ray tube is adapted to filter the resulting X-radiation for eliminating at least partially a poorly polarized spectral portion of said at least partially polarized X-radiation.

4. An X-ray tube as set forth in claim 3, wherein the anode is made completely of beryllium.

5. An X-ray tube as set forth in claim 3, wherein the X-ray tube housing is adapted to filter the resulting X-radiation for eliminating at least partially a poorly polarized spectral portion of said at least partially polarized X-radiation.

6. An X-ray tube as set forth in claim 3, wherein, in addition to the housing, the X-ray tube includes at least one filtering material layer.

7. The use of a beryllium-anode equipped X-ray tube for producing polarized X-radiation.

* * * * *